United States Patent [19]
Van Doorn et al.

[11] Patent Number: 6,005,063
[45] Date of Patent: Dec. 21, 1999

[54] EPOXY COMPOUNDS FROM CHLOROHYDRIN ETHERS OF POLYPHENOLS

[75] Inventors: Johannes Adrianus Van Doorn; Jozef Jacobus Titus Smits; Eric Johannes Vos, all of Amsterdam, Netherlands

[73] Assignee: Shell Oil Company, Houston, Tex.

[21] Appl. No.: 09/019,544

[22] Filed: Feb. 6, 1998

[30] Foreign Application Priority Data

Feb. 7, 1997 [EP] European Pat. Off. .............. 97200328

[51] Int. Cl.$^6$ ........................ C07C 43/225; C08G 59/02; C08G 65/38
[52] U.S. Cl. .............................. 528/86; 549/40; 549/230; 568/641; 568/643; 568/645; 568/649; 528/92
[58] Field of Search ..................... 549/40, 230; 568/641, 568/643, 645, 649; 528/86, 92

[56] References Cited

U.S. PATENT DOCUMENTS

| | | |
|---|---|---|
| 2,856,413 | 10/1958 | Malkemus et al. ..................... 260/348 |
| 3,033,820 | 5/1962 | Price et al. . |
| 3,071,562 | 1/1963 | Price et al. . |
| 3,162,615 | 12/1964 | Bremmer . |

FOREIGN PATENT DOCUMENTS

| | | |
|---|---|---|
| 0047473 | 9/1981 | European Pat. Off. . |
| 57-77682 | 5/1982 | Japan . |
| 61-33180 | 2/1986 | Japan . |

OTHER PUBLICATIONS

Braun, "On some side products during the formation of epoxy resins from bisphenol A and epichlorohydrin," Angew. Makromol. Chem., vol. 51, No. 1, pp. 11–24, 1976.

Gasan–Zade et al., "Use of the multiple attenuated total internal reflection method for studying the synthesis of epoxy resins," Lakokras. Mater. Ikh Primen., vol. 5, pp. 11–13, 1976.

*Primary Examiner*—Robert E. Sellers

[57] ABSTRACT

Process for the preparation of compound of the formula:

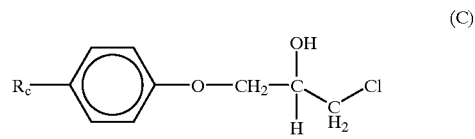

(C)

wherein $R_c$ represents a residue comprising one or more additional groups of the formula:

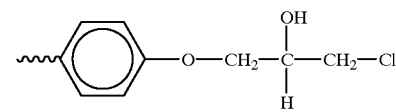

by heating a compound of the formula (A)

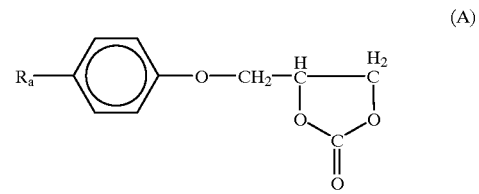

(A)

or

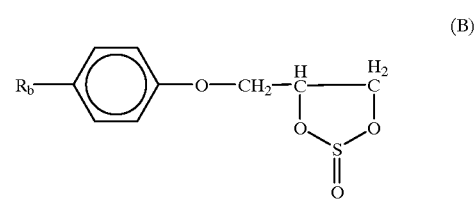

(B)

at a temperature in the range of from 120 to 220° C. in the presence of hydrogen halide addition salt of tertiary amine;

process for the preparation of epoxy compounds starting from the reaction of a polyphenol compound and glycidol; and epoxy resins obtained by this process showing a significantly lower content of intermingled clorine and being substantially free of usual build-up products.

5 Claims, 2 Drawing Sheets

EPOXY COMPOUNDS FROM CHLOROHYDRIN ETHERS OF POLYPHENOLS

The invention is relating to a process for the manufacture of epoxy compounds. More in particular the invention is relating to a process for the manufacture of epoxy compounds without the involvement of halogen and in particular chlorine gas.

BACKGROUND OF THE INVENTION

Epoxy compounds, which are manufactured in a great variety on large industrial scales throughout the world, are used for an extensive scale of end applications, such as the manufacturing of shaped articles, including embedded small electronic components such as semi-conductors or chips and the prepregs for the subsequent manufacture of printed circuits for the electronic industry, coatings including the organic solvent based coatings as well as the more modern aqueous epoxy resin dispersion coatings, and in particular can and drum coatings, composites and laminates showing great flexibility, and the like.

Said starting epoxy compounds were manufactured up to now by means of the starting reagent epihalohydrin and in particular epichlorohydrin, which in its turn was manufactured via allylchloride, prepared from propene and gaseous chlorine.

It will be appreciated that on the one hand, there has been developed in the last decade and in particular in the last five years, an increasing pressure from national or regional governmental regulations and requirements to chemical process industry, in order to drastically reduce possible chlorine emissions or even to avoid the use of chlorine completely, and on the other hand, in the current manufacturing processes for chlorination of propene in the gaseous phase there is still a need to improve the relatively low yield and to diminish the high fouling tendency.

Moreover, during the reaction of epihalohydrin with phenolic compounds to form epoxy resin it is not possible to avoid completely that halogen, originating from the epihalohydrin, is intermingled in a resin as a product in the form that the halogen atom is chemically bound to the epoxy resin itself. As one of the important applications of the epoxy resin is encapsulation of micro electronic material, it will be appreciated that this intermingled halogen liberates as an acid by moisture, during use of the final article for a long period of time and this acid leads to corrosion of a metal material.

Therefore one object of the present invention is formed by a process, meeting the requirements of the present environmental legislation and that one presumably enforced in the near future, and starting from cheap and generally available basic chemicals.

One of the alternative manufacturing routes for epoxy resins, proposed in the past was that according the following simplified reaction scheme:

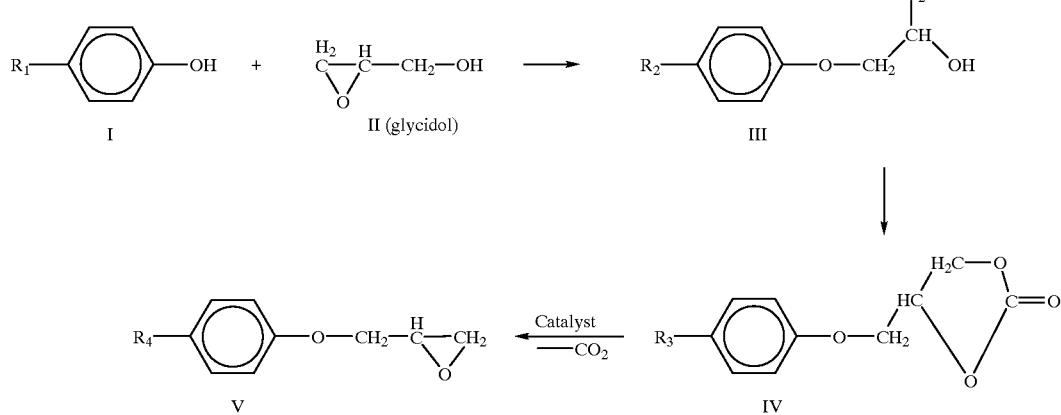

transesterification with e.g. alkylene carbonate ($C_1$–$C_4$ alkyl), cycloalkylene carbonate, arylalkylene carbonate or dialkylene carbonate ($C_1$–$C_4$ alkyl) and preferably propylene carbonate+alkyleneglycol, cycloalkylene glycol or arylalkylene glycol, and preferably propylene glycol, wherein $R_1$ represents a residue comprising one or more additional phenol groups, wherein $R_2$ represents a residue comprising one or more additional groups of the formula:

VI

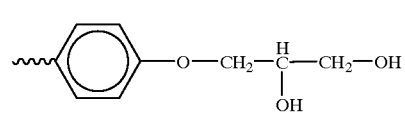

wherein $R_3$ represents a residue comprising one or more additional groups of the formula:

VII

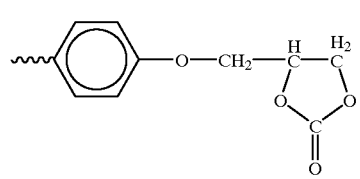

and wherein $R_4$ represents a residue comprising one or more additional groups

VIII

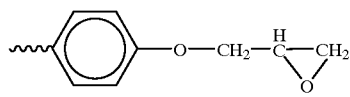

Although it was already known from e.g. Japanese patent application Sho 61-33180 A, to produce epoxy compounds by decarboxylating a carbonate compound, using as catalyst a combination of an alkali metal halide and of a dihydrogenphosphate of an alkali metal while earlier proposed similar processes were known from e.g. JP-Sho-57-77682 A and U.S. Pat. No. 2,856,413, said route could not be used for economical manufacture of epoxy compounds up to now.

In particular from JP-Sho-61-33180 it will be appreciated that the finally obtained mono-epoxy compounds had such a simple molecular structure, that they could be recovered from the initially crude reaction mixture by distillation.

However such a distillation has appeared to be not possible for the commercial standard difunctional and multifunctional epoxy compounds aimed at.

Therefore there was still a strong need for improvement of this proposed route to enable industrial scale manufacture at all.

DETAILED DESCRIPTION OF THE INVENTION

Figure 1:
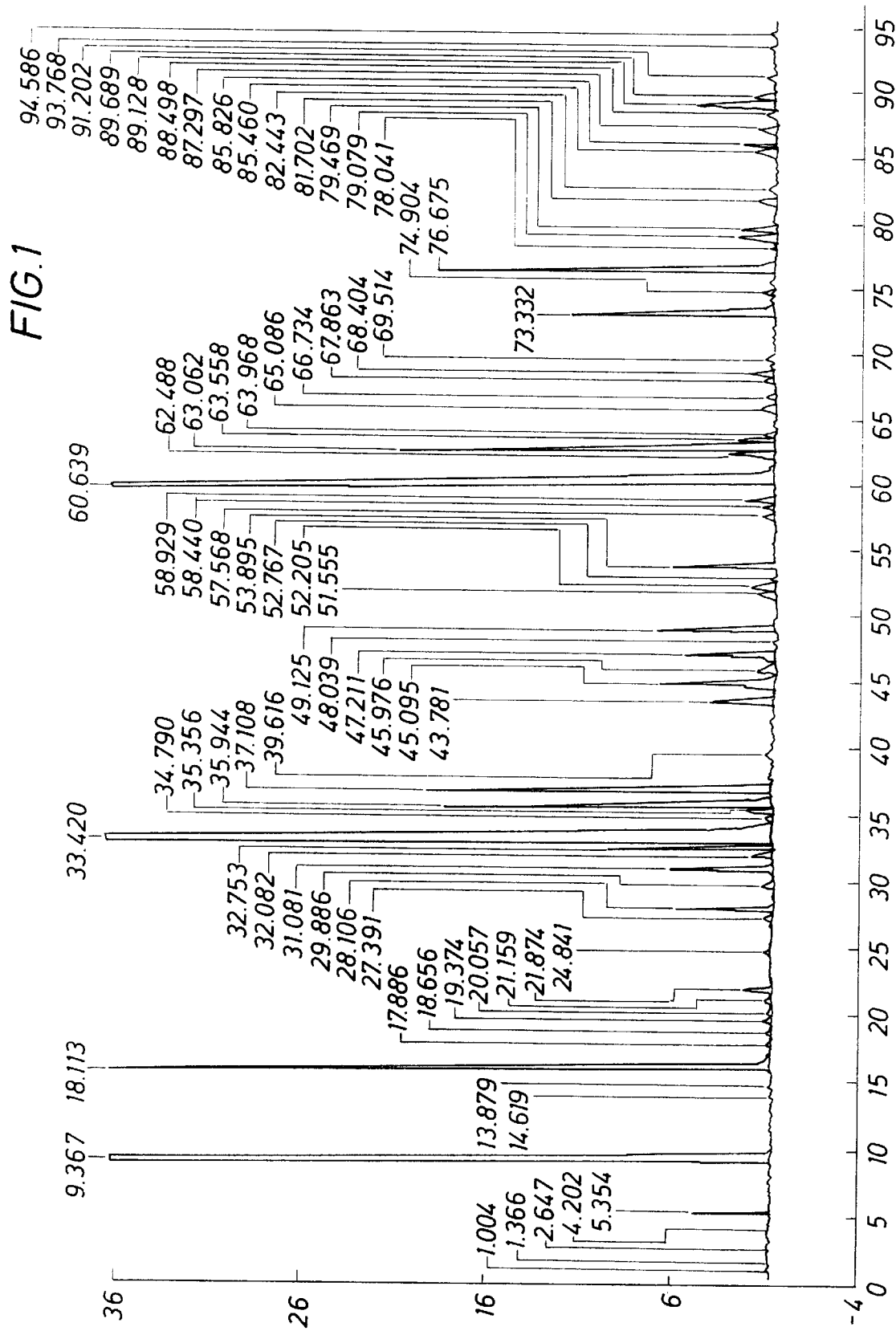
FIG. 1 is a chromatograph of the high-pressure liquid chromatography (HPLC) analysis of Epikote 282 epoxy resin.

As a result of extensive research and experimentation it has now been surprisingly found, that compounds of the formula

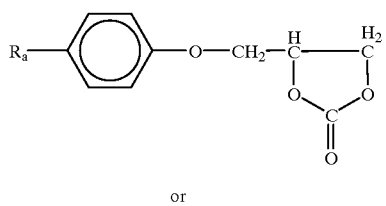

or

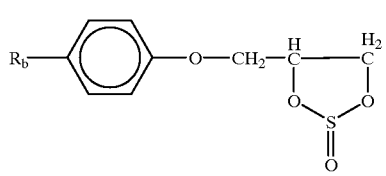

wherein $R_a$ represents a residue, comprising one or more additional groups of the formula VII and wherein $R_b$ represents a residue comprising one or more additional groups of the formula

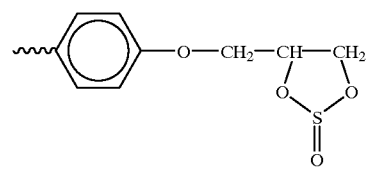

can be very efficiently converted into compounds of the formula

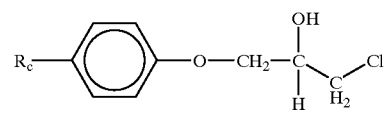

and $CO_2$ or $SO_2$ respectively wherein $R_c$ represents a residue comprising one or more additional groups of the formula:

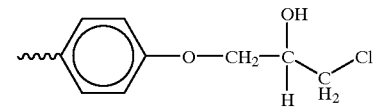

by heating at a temperature in the range of from 120 to 220° C. and preferably from 140 to 200° C. in the presence of a hydrogen halide addition salt of a tertiary amine $N(R_1R_2R_3)$ as catalyst wherein each of the symbols $R_1$, $R_2$ and $R_3$ may independently represent an alkyl group of from 1 to 10 carbon atoms and preferably from 1 to 5 carbon atoms, an aryl group and preferably a phenyl group, an aralkyl group having from 1 to 5 carbon atoms in its alkyl group and preferably benzyl or phenyl ethyl, a cycloalkyl group having from 5 to 10 carbon atoms or an alkylcycloalkyl having from 1 to 6 carbon atoms in its alkyl group.

The hydrogen halide to be used for the addition to the amine for formation of the catalyst can be selected from hydrogen chloride, hydrogen bromide or hydrogen iodide, but preferably hydrogen chloride is used.

Preferably tertiary amine addition salts derived from HCl and trialkylamine such as trimethylamine, triethylamine, tri-n-propylamine, triisopropylamine, tri(n-butyl)amine or tri(isobutyl)amine, and more preferably salts derived from HCl and triethylamine or triethylamine are used as catalysts.

The period of heating the compound A or B at the hereinbefore specified temperature will normally be in the range from 0.5 to 2 hours and preferably from 0.5 to 1 hour.

It will be appreciated that the product obtained according to this process step, can indeed be quantitatively converted into the corresponding epoxy compound

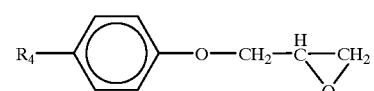

by a known process step, using a temperature in the range of from 10 to 120° C. and preferably from 40 to 70° C., in a polar solvent and preferably a ketone such as methyl isobutyl keton (MIBK) or toluene and using an alkali compound, such as NaOH, providing epoxy resins with an epoxy group content (EGC) of at least 5000 mmol/kg. It will be appreciated that the significantly improved process step of the present invention has formed a bottleneck in the hereinbefore depicted complete reaction scheme for some time, making the alternative route much less attractive.

It will be appreciated that not only relatively simple compounds, such as

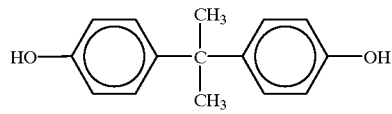

can be used as starting material of formula I in the above depicted scheme but also polymeric compounds, containing a greater number of phenolic groups which may partially or completely be converted into the groups of formula (VIII).

I.e. the simple standard epoxy compound of formula

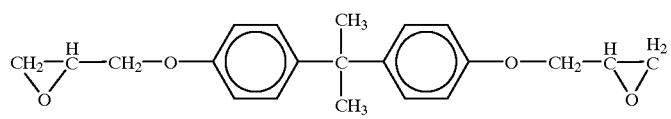

can be prepared according to the process of the present invention, but also a multifunctional epoxy compound, having a much more complicated structure can be prepared.

For example in this respect, a great variety of phenol-formaldehyde resins can be used as starting material I (novolac resins).

It was known for a long time to carry out the industrial scale manufacture of compound I starting from a ketone and phenol, providing cheap products.

An important representative of compound I, having a rather simple structure is DPP(diphenylolpropane).

Also the reagent II (glycidol) can be regarded as a relative cheap product prepared from propene.

The process step from compounds (B) to compounds (C) of the present invention has been surprisingly found to be not possible at all when using as catalyst only hydrogen halide either as a gas or as an aqueous solution.

It will be appreciated that the invention is also relating to a complete integrated manufacturing process for the final epoxy resins comprising the hereinbefore specified improved process step and starting from a polyphenol compound (I), such as DPP for standard commercial epoxy resins, and glycidol (II).

Accordingly the invention also relates to a process for the manufacture of epoxy compounds comprising the steps of (a) reaction of a compound

I wherein $R_1$ represents a residue comprising one or more additional phenol groups, with a compound

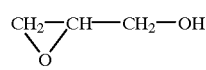

II in the presence of a polar compound, such as a ketone or a mixture of ketone with an alkanol having from 1 to 6 carbons, and in the presence of an alkali compound such as NaOH, at a temperature of from 30 to 110° C., and preferably from 60 to 100° C. to form a compound of the formula:

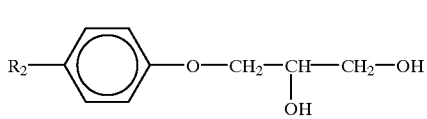

III wherein $R_2$ represents a residue comprising one or more additional groups of the formula

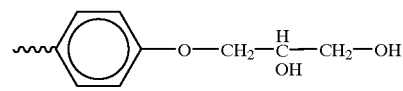

b) conversion of the compound of formula III obtained in step (a), into a compound of the formula:

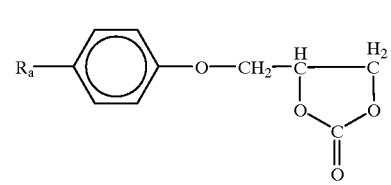

(A)

or

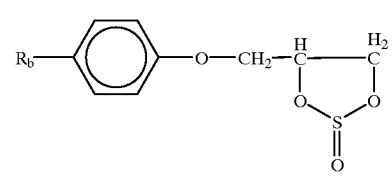

(B)

wherein $R_a$ represents a residue, comprising one or more additional groups of the formula:

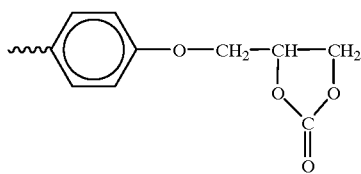

(A')

and wherein $R_b$ represents a group a residue comprising one or more additional groups of the formula

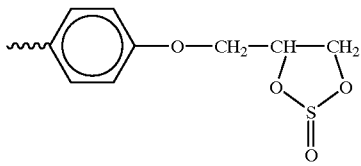

(B')

by transesterification with an alkylene carbonate or alkylene sulfite, having 1 to 4 carbon atoms alkylene group, a cycloalkylene carbonate or cycloalkylene sulfite, arylalkylene carbonate or aralkylene sulphite, or dialkylene carbonate or dialkylene sulphite by heating to a temperature in the range of from 90 to 160° C. in the presence of an alkali compound such as aqueous NaOH solution.

c) conversion of said compound of formula A or B into a compound of the formula

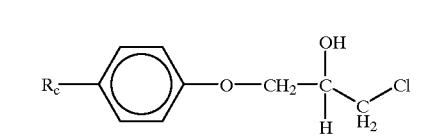

(C)

and $CO_2$ or $SO_2$ respectively, wherein $R_c$ represents a residue comprising one or more additional groups of the formula:

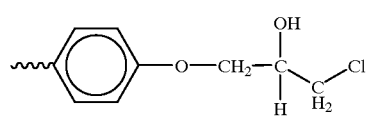

(C')

by heating at a temperature in the range of from 120 to 220° C. and preferably from 140 to 200° C. in the presence of a hydrogen halide addition salt of a tertiary amine $N(R_1R_2R_3)$ as catalyst wherein each of the symbols $R_1$, $R_2$ and $R_3$ may independently represent an alkyl group of from 1 to 10 carbon atoms and preferably from 1 to 5 carbon atoms, an aryl group and preferably a phenyl group, an aralkyl group having from 1 to 5 carbon atoms in its alkyl group and preferably benzyl or phenyl ethyl, a cycloalkyl group having from 5 to 10 carbon atoms or an alkylcycloalkyl having from 1 to 6 carbon atoms in its alkyl group.

(d) conversion of the compound of formula C into an epoxy compound of formula

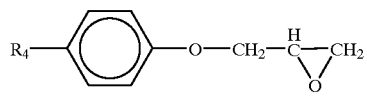

V wherein $R_4$ represents a residue comprising one or more additional groups

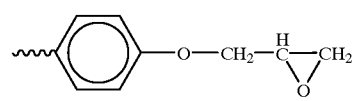

VIII at a temperature in the range of from 10 to 120° C., in a polar solvent and using an alkali compound.

Preferably the reaction step (d) is carried out in a ketone such as methyl isobutyl ketone (MIBK) or toluene and using NaOH as alkali. More preferably an aqueous NaOH solution is used of 40 to 70 wt %.

Another aspect of the present invention is formed by the final epoxy resins which are obtainable by the complete manufacturing process as specified hereinbefore and which do contain significantly less intermingled halogen, and in particular chlorine, (at most 1800 ppm) and substantially no build-up products (compounds) which are normally present in conventionally produced epoxy resins produced from a bisphenol and epihalohydrin of the formula

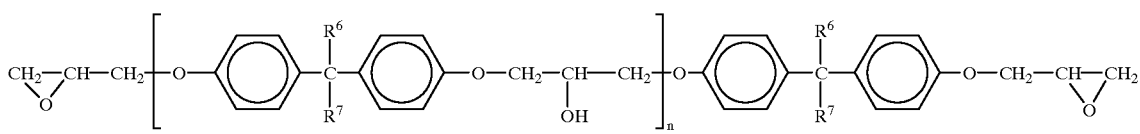

wherein $R^6$ and $R^7$ may represent lower alkyl, and preferably methyl, or hydrogen and wherein n=1, n=2 etc.

Said epoxy resins are characterized by HPLC analysis. The chromatogram clearly shows the absence of the so-called build-up products (n=1, n=2, etc.), which are normally present in conventional epoxy resins prepared from e.g. bisphenol A and epichlorohydrin, related to peaks at 60.7 and 76.8, whereas some extra peaks emerge in the chromatogram as can be derived from the chromatograms in FIGS. 1 and 2, which were performed under the conditions as described in Example X.

The invention is further illustrated by the following examples and comparative examples, however, without restricting its scope to these specific embodiments.

Preparation of the di-α-glycol ether of DPP

In a 100 ml three-necked round-bottom flask equipped with a reflux condenser and an thermocouple, 22.84 gram (0.100 mmol) diphenylolpropane (DPP or bisphenol A) and 15,54 gram glycidol (0.210 mol) is dissolved in 15.05 gram (0.150 gram (0.150 mol) methyl-isobutylketone (MIBK) and 15.04 (0.25 mol) isopropylalcohol (IPA). At 80° C., 6 mol % of an aqueous NaOH solution (50 wt %) was added at once. The mixture was maintained at 80° C. for 6 hours. Then, the solvent was removed in vacuo. The di-α-glycol ether of DPP is obtained as a white solid material (33.9 gram, 89.5%).

The procedure of this preparation was repeated with variations as depicted in the table:

| | glycidol/DPP molar ratio | solvent (mol %) | temp. (° C.) | catalyst (mol %) | diαgc (mol %) | 1,2-1,3 (mol %) | 1,2-OH (mol %) | build-up |
|---|---|---|---|---|---|---|---|---|
| 1 | 2.2 | MIKB 300 | 90 | NaOH 2 | 85.7 | 4.9 | 0.0 | 9.1 |
| 2 | 2.1 | MIKB 300 | 90 | NaOH 2 | 87.9 | 4.6 | 2.6 | 4.9 |
| 3 | 2.1 | MIKB 300 | 70 | NaOH 6 | 89.6 | 3.9 | 2.5 | 4.0 |
| 4 | 2.1 | MIKB 300 | 90 | NaOH 2 | 88.2 | 4.7 | 1.9 | 5.2 |
| 5 | 2.1 | MIKB 150 IPA 250 | 80 | NaOH 6 | 89.5 | 4.1 | 1.7 | 4.7 |
| 6 | 2.1 | MIKB 270 IPA 45 | 70 | NaOH 6 | 88.0 | 3.7 | 2.3 | 6.1 |
| 7 | 2.1 | MIKB 180 IPA 35 | 70 | NaOH 6 | 87.0 | 3.8 | 4.4 | 4.8 |

If the reaction is performed in pure MIBK (without IPA as a co-solvent), the di-α-glycol ether of DPP crystalizes after cooling down.

Preparation of the bis-cyclic carbonate ester of DPP

A 100 ml round-bottom flask is charged with 20.0 gram of the di-α-glycol ether of DPP (89% pure, 47.3 mmol) and 28.58 gram (0.280)propylene carbonate (PC). The mixture is heated at 100° C. and 2 mol % of an aqueous NaOH solution (50 wt %) is added. After 1 hour, a vacuum is applied to remove the formed propanediol and excess propylene carbonate (final conditions 160° C., 20 mbar). The yield of the crystalline material is 22.4 gram.

Preparation of the bis-chlorohydrin ether of DPP

EXAMPLE 1

A 100 ml three-necked round-bottom flask is charged with 21.40 (0.05 mol) of the biscycliccarbonate ester of DPP and with 13.75 gram (0.1 mol) of the HCl salt of triethylamine. The mixture is heated and a vacuum of 300 mbars is applied. At 140° C., triethylamine is distilled off and the temperature is raised in 15 minutes to 180° C. and then to 200° C. The mixture is held at 200° C. for 10 minutes. The total reaction time has been 30 minutes. The conversion to the bis-chlorohydrin ether of DPP is 92% (selectivity more than 95%). Side products are ketones (about 1%) and epoxides (about 2%).

EXAMPLE II

The same procedure as in example I is used, but the distillation is continued for 45 minutes at a lower pressure (100 mbar). The conversion is 100%, the selectivity to the bis-chlorohydrin ether of DPP is more than 96% (same side products).

EXAMPLE III

A 100 ml three-necked round-bottom flask is charged with 11.71 (25 mmol) of the bis-cyclic sulphite ester of DPP and with 6.88 gram (50 mmol) of the HCl salt of triethylamine (Net3.HCl). The mixture is heated and a vacuum of 300 mbars is applied. At 140° C., triethylamine is distilled off and the temperature is raised in 15 minutes to 180° C. and then to 200° C. The mixture is held at 200° C. for 20 minutes. The total reaction time has been 40 minutes. The conversion to the bis-chlorohydrin ether of DPP is 95% (selectivity more than 95%). Side products are epoxides (about 2%).

EXAMPLE IV

The same procedure as in example I, but with the tri-methylamine HCl salt. The total reaction time has been 30 minutes. The conversion to the bis-chlorohydrin ether of DPP is 94% (selectivity more than 95%). Side products are ketones (about 1%) and epoxides (about 2%).

EXAMPLE V

The same procedure as in example II, but with the tri-propylamine HCl salt The conversion to the bis-chlorohydrin ether of DPP is 90% (selectivity more than 95%). Side products are ketones (about 1.5%) and epoxides (about 2.5%).

COMPARATIVE EXAMPLE I

A 100 ml three-necked round-bottom flask is charged with 21.40 (0.05 mol) of the bis-carbonate ester. At 100° C. a continuous stream of HCl gas is passed through the flask for 4 hours. The conversion of the bis-carbonate ester is less than 5%.

COMPARATIVE EXAMPLE II

A 100 ml three-necked round-bottom flask is charged with 10.7 (0.025 mol) of the bis-carbonate ester dissolved in 40 ml toluene, and 40 ml of an aqueous HCl solution is added. The mixture is stirred at 50° C., 2 hours. The conversion of the bis-carbonate ester is less than 5%.

The reaction was also attempted at other temperature (−10° C., 0° C., 20° C. and reflux) with similar results.

Preparation of the bis-bromohydrin ether of DPP

EXAMPLE VI

The same procedure as in Example II, but the HBr salt of tri-ethylamine is used (NEt3HBr). The product in this case is the bromohydrin ether of DPP. Conversion is 100%, selectivity over 95%. Side products are epoxides, no ketone could be observed.

EXAMPLE VII

The same procedure as in Example III, but with Net$_3$HBr. The conversion is almost 100%, the selectivity is over 95%.

EXAMPLE VIII

The same procedure as in Example VI, but with the tri-methylamine HBr salt The total reaction time has been 30 minutes. The conversion to the bis-bromohydrin ether of DPP is 96% (selectivity more than 95%). Side products are (among others) ketones (about 1.5%) and epoxides (about 2%).

EXAMPLE IX

The same procedure as in Example I, but with the tri-ethylamine HI salt. The total reaction time has been 30 minutes. The conversion to the bis-iodohydrin ether of DPP is 89% (selectivity more than 90%). Side products are ketones (about 4%) and epoxides (about 4%).

Preparation of the diglycidyl ether of DPP

The conversion of the bis-chlorohydrine ether of DPP (3) to an epoxy resin can be achieved via a conventional treatment with base in a suitable solvent.

EXAMPLE X 20.63 Gram (47.9 mmol) of the bis-chlorohydrine ether of DPP is dissolved in 64 gram MIBK and heated to 85° C. Then, a solution of 6 gram (0.15 mol) NaOH in 34 gram water is added at once, and the mixture is vigorously stirred for 1 hour. After phase separation the MIBK layer is washed twice with 20 grams water. The MIBK is evaporated in vacuo to yield 13.3 gram (83%) of an Epikote 828 type of resin with an epoxy group content (EGC) of 5070 mmol/Kg.

Figure 2:
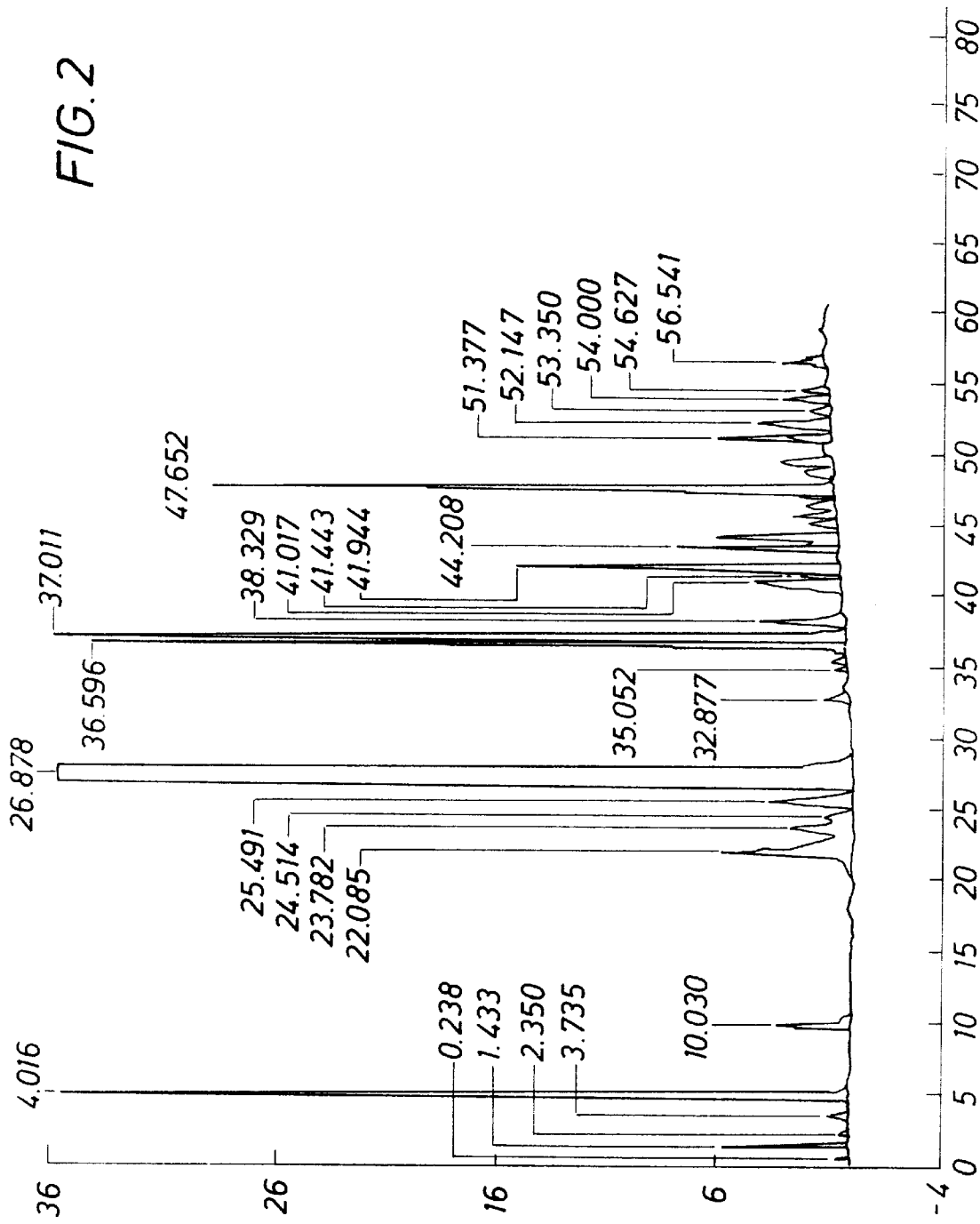
FIG. 2 is a chromatograph of the HPLC analysis of the product obtained in following Example X.

A HPLC analysis of the obtained product provided FIG. 2, using a HP 1090 liquid chromatograph and dissolving 2.0 g of the resin into 20 g of acetonitrile and using anisole as an internal standard. The analysis was performed using a NOVOPACK C18 column, 15 cm×3.9 cm, using a flow of 1 ml/min. and an injection volume of 1 microliter and an initial solvent composition consisting of 75% wt of water and 25% wt acetonitrile. A solvent gradient was used.

In 110 minutes the composition changed linear to 6.5% water and 93.5% acetonitrile.

At 115 minutes: 0% water and 100% acetonitrile and at 125 minutes 75% water and 25% acetonitrile.

The analysis was performed at 50° C. with UV detection at 275 nm.

Under the same conditions a chromatogram was performed from a standard EPIKOTE 828 resin (FIG. 1).

Alternatively, other bases can be used such as metal hydroxides (for instance KOH, LiOH, Ca(OH)$_2$, Mg(OH)$_2$), metal carbonates (Na$_2$CO$_3$, K$_2$CO$_3$), tertiary amines, NH$_4$OH etc. Also other solvents can be used, for instance toluene, xylene, MEK, CH$_2$Cl$_2$, diethyl ether, etc.

COMPARATIVE EXAMPLE III

Direct conversion of bis-carbonate ester of DPP in the diglycidyl ether of DPP.

Efforts were made to convert the bis-carbonate ester of DPP directly in the diglycidyl ether of DPP, using the procedure described in JP-SHO-61-33180. The reaction was performed at 250° C. and a vacuum was applied. In the beginning of the reaction (first 25 minutes) the lowest pressure obtainable was 4 mbar due to CO$_2$ formation. Hereafter, the vacuum was 1 mbar. The temperature was raised to 270° C. About 50% of the material was distilled. NMR analysis of the distillate showed the presence of ketone end-groups instead of epoxy end groups. The residue also contained ketone end groups and oligomeric structures, no epoxy end groups.

We claim:

1. A process for the preparation of compound of the formula:

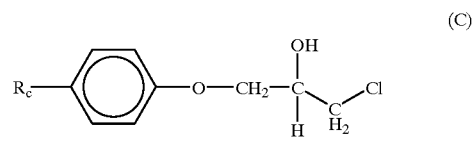

(C)

wherein R$_c$ represents a residue comprising at least one additional groups of the formula:

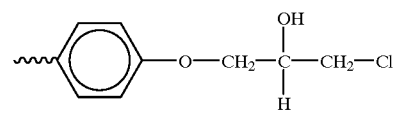

by heating a compound of the formula (A)

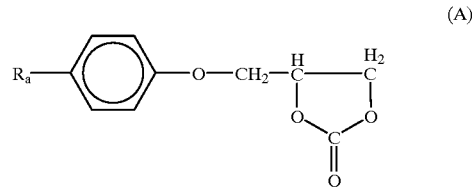

(A)

or

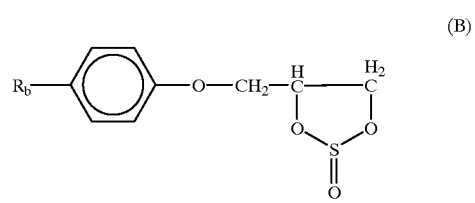

(B)

wherein R$_a$ represents a residue, comprising at least one additional groups of the formula

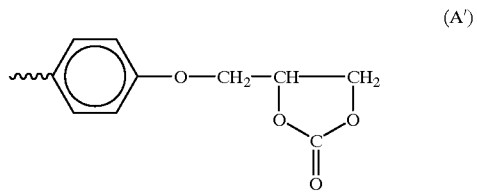

(A')

and wherein R$_b$ represents a residue, comprising at least one additional groups of the formula

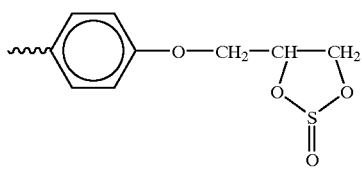

(B')

at a temperature in the range from 120 to 220° C., in the presence of a hydrogen halide addition salt of a tertiary amine $N(R_1, R_2, R_3)$ as catalyst, wherein each of the symbols $R_1$, $R_2$, and $R_3$ may independently represent an alkyl group of from 1 to 10 carbon atoms, an aryl group, an aralkyl group having from 1 to 5 carbon atoms in its alkyl group, a cycloalkyl group having from 5 to 10 carbon atoms, or an alkylcycloalkyl having from 1 to 6 carbon atoms in its alkyl group.

2. The process of claim 1 wherein the catalyst is a hydrogen chloride addition salt of a tertiary amine.

3. The process of claim 2 wherein the catalyst is a hydrogen chloride addition salt of trimethylamine or triethylamine is used as catalyst.

4. The process of claim 1 wherein the temperature is within the range of from 140 to 200° C.

5. The process of claim 1 wherein the heating period is in the range of from 0.5 to 2 hours.

* * * * *